(12) United States Patent
Yamada

(10) Patent No.: US 10,568,705 B2
(45) Date of Patent: *Feb. 25, 2020

(54) MAPPING IMAGE DISPLAY CONTROL DEVICE, METHOD, AND PROGRAM

(71) Applicant: FUJIFILM Corporation, Tokyo (JP)

(72) Inventor: Kenta Yamada, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 105 days.

This patent is subject to a terminal disclaimer.

(21) Appl. No.: 15/909,377

(22) Filed: Mar. 1, 2018

(65) Prior Publication Data

US 2018/0185101 A1 Jul. 5, 2018

Related U.S. Application Data

(63) Continuation of application No. PCT/JP2016/068562, filed on Jun. 22, 2016.

(30) Foreign Application Priority Data

Sep. 9, 2015 (JP) .................. 2015-177523

(51) Int. Cl.
*A61B 34/00* (2016.01)
*G06T 17/00* (2006.01)
(Continued)

(52) U.S. Cl.
CPC .............. *A61B 34/25* (2016.02); *A61B 6/466* (2013.01); *A61B 6/481* (2013.01); *A61B 6/50* (2013.01);
(Continued)

(58) Field of Classification Search
None
See application file for complete search history.

(56) References Cited

U.S. PATENT DOCUMENTS

| | | | |
|---|---|---|---|
| 8,374,410 B2* | 2/2013 | Ohyu | A61B 6/463 382/128 |
| 9,144,407 B2* | 9/2015 | Nakamura | A61B 6/032 |

(Continued)

FOREIGN PATENT DOCUMENTS

| | | |
|---|---|---|
| JP | 2006-81906 A | 3/2006 |
| JP | 2010-517633 A | 5/2010 |

(Continued)

OTHER PUBLICATIONS

International Preliminary Report on Patentability and Written Opinion of the International Searching Authority (Forms PCT/IB/326, PCT/IB/373 and PCT/ISA/237) for Application No. PCT/JP2016/068562, dated Mar. 22, 2018, with an English translation.

(Continued)

*Primary Examiner* — Samah A Beg
(74) *Attorney, Agent, or Firm* — Birch, Stewart, Kolasch & Birch, LLP

(57) ABSTRACT

A mapping image display control device includes a lung region extraction unit 11 that extracts a lung region included in a three-dimensional image, a bronchus region extraction unit 12 that extracts a bronchus region included in the lung region, a branching position information acquisition unit 13 that acquires information about a branching position of the bronchus region, a reaching position information estimation unit 14 that estimates reaching position information about a position at which an extended line of a branch included in the bronchus region reaches a surface of the lung region on the basis of the information about the branching position, and a display control unit 15 that generates a mapping image in which the reaching position information is mapped to the surface of the lung region and that causes a display apparatus 3 to display the mapping image.

17 Claims, 9 Drawing Sheets

(51) Int. Cl.
*G06T 7/11* (2017.01)
*G06T 7/00* (2017.01)
*G06T 19/20* (2011.01)
*A61B 6/00* (2006.01)
*G06T 7/187* (2017.01)
*A61B 34/10* (2016.01)
*A61B 34/20* (2016.01)
*A61B 6/03* (2006.01)
*A61B 5/055* (2006.01)
*A61B 17/00* (2006.01)

(52) U.S. Cl.
CPC ............ *A61B 6/5217* (2013.01); *A61B 34/10* (2016.02); *A61B 34/20* (2016.02); *G06T 7/0012* (2013.01); *G06T 7/11* (2017.01); *G06T 7/187* (2017.01); *G06T 17/00* (2013.01); *G06T 19/20* (2013.01); *A61B 5/055* (2013.01); *A61B 6/032* (2013.01); *A61B 6/4405* (2013.01); *A61B 2017/00809* (2013.01); *A61B 2034/104* (2016.02); *A61B 2034/105* (2016.02); *A61B 2034/2065* (2016.02); *G06T 2200/04* (2013.01); *G06T 2207/10024* (2013.01); *G06T 2207/10081* (2013.01); *G06T 2207/10088* (2013.01); *G06T 2207/30061* (2013.01); *G06T 2207/30096* (2013.01)

(56) References Cited

U.S. PATENT DOCUMENTS

| | | | | |
|---|---|---|---|---|
| 9,713,504 | B2* | 7/2017 | Itai | A61B 6/504 |
| 10,198,875 | B2* | 2/2019 | Yamada | A61B 6/03 |
| 2005/0207630 | A1* | 9/2005 | Chan | A61B 6/466 |
| | | | | 382/131 |
| 2006/0056685 | A1* | 3/2006 | Kiraly | G06T 7/0012 |
| | | | | 382/165 |
| 2008/0183073 | A1* | 7/2008 | Higgins | G06T 19/003 |
| | | | | 600/425 |
| 2011/0190626 | A1* | 8/2011 | Mizuno | G06T 7/0012 |
| | | | | 600/425 |
| 2011/0237938 | A1* | 9/2011 | Mizuno | G06T 7/0012 |
| | | | | 600/425 |
| 2011/0243403 | A1* | 10/2011 | Mizuno | G06T 7/0012 |
| | | | | 382/128 |
| 2013/0009958 | A1* | 1/2013 | Kitamura | A61B 6/032 |
| | | | | 345/424 |
| 2014/0079306 | A1* | 3/2014 | Inoue | G06T 7/12 |
| | | | | 382/131 |
| 2014/0341426 | A1* | 11/2014 | Wu | G06T 7/187 |
| | | | | 382/103 |
| 2015/0029184 | A1* | 1/2015 | Masumoto | G06T 19/00 |
| | | | | 345/419 |
| 2015/0187085 | A1* | 7/2015 | Ihara | A61B 5/08 |
| | | | | 382/128 |
| 2015/0187118 | A1* | 7/2015 | Masumoto | A61B 6/468 |
| | | | | 345/419 |
| 2018/0140359 | A1* | 5/2018 | Koyrakh | A61B 34/10 |
| 2018/0225884 | A1* | 8/2018 | Yamada | A61B 6/03 |
| 2018/0240232 | A1* | 8/2018 | Wang | G06T 7/11 |
| 2018/0243034 | A1* | 8/2018 | Yamada | A61B 5/08 |

FOREIGN PATENT DOCUMENTS

| | | |
|---|---|---|
| JP | 2014-223311 A | 12/2014 |
| WO | WO 2010/086909 A1 | 8/2010 |
| WO | WO 2014/045539 A1 | 3/2014 |

OTHER PUBLICATIONS

International Search Report and English translation (Form PCT/ISA/210) for Application No. PCT/JP2016/068562, dated Sep. 27, 2017.

Sato et al., "Thoracoscopic wedge lung resection using virtual-assisted lung mapping," Asian Cardiovascular and Thoracic Annals, URL:http://aan.sagepub.com/content/early/2014/06/12/0218492314539332, Jun. 12, 2014, pp. 1-9 (10 pages total).

* cited by examiner

MAPPING IMAGE DISPLAY CONTROL DEVICE, METHOD, AND PROGRAM

CROSS-REFERENCE TO RELATED APPLICATIONS

This application is a Continuation of PCT International Application No. PCT/JP2016/068562 filed on Jul. 22, 2016, which claims priority under 35 U.S.C § 119(a) to Japanese Patent Application No. 2015-177523 filed on Sep. 9, 2015. Each of the above application(s) is hereby expressly incorporated by reference, in its entirety, into the present application.

BACKGROUND OF THE INVENTION

1. Field of the Invention

The present invention relates to a device, method, and a computer readable non-transitory recording medium storing a program for simulating positions on the lung surface at which dye seeps if the dye is sprayed into the peripheries of bronchi and for generating and displaying a mapping image in which the positions are mapped to the lung surface.

2. Description of the Related Art

VAL-MAP (Virtual Assisted Lung Mapping) has been recently proposed as a method for marking a resection region of the lung (see Masaaki Sato and eight others, "Thoracoscopic wedge lung resection using virtual-assisted lung mapping", [online], Jun. 12, 2014, Asian Cardiovascular and Thoracic Annals, <URL:http://aan.sagepub.com/content/early/2014/06/12/0218492314539332>). In VAL-MAP, each bronchus located near a tumor is selected in a given manner and a bronchoscopic procedure is performed in the bronchus. Then, a catheter is advanced up to the periphery of the bronchus, and dye is sprayed into the periphery to stain the lung surface.

Staining the lung surface in this way enables highly accurate prediction of the location of a tumor by using the stained regions as landmarks at the time of a procedure of thoracotomy or thoracoscopy.

SUMMARY OF THE INVENTION

When performing VAL-MAP described above, doctors sometimes desire to confirm which part of the lung surface is stained if which bronchus is selected and dye is sprayed thereinto, through a simulation prior to the procedure. Accordingly, methods for simulating stainable positions on the lung surface on the basis of bronchus regions extracted by image processing are conceivable.

In the case of performing such a simulation, it is conceivable to extend a bronchus region to the lung surface since the bronchus region usually does not extend to be in contact with the lung surface. As a method for extending a bronchus region to the lung surface, a method for extracting a path of a bronchus region as a graph structure and extending the end of the graph structure to the lung surface is conceivable.

However, when the extraction accuracy of a bronchial path based on image processing is low, the bronchial path is incorrectly recognized. As a result, the end of the graph structure may bend in an unnatural direction. In such a case, since an extending direction of the end of the graph structure also becomes unnatural and is different from an actual extending direction of the bronchus region, a to-be-stained position on the lung surface cannot be simulated at a high accuracy.

In view of the circumstance described above, an object of the present invention is to provide a mapping image display control device, method, and a computer readable non-transitory recording medium storing a program that can simulate, at a high accuracy, positions on the lung surface at which dye seeps if the dye is sprayed into the peripheries of bronchi and generate and display a mapping image in which the positions are mapped.

A mapping image display control device according to an aspect of the present invention includes a lung region extraction unit that extracts a lung region included in a three-dimensional image, a bronchus region extraction unit that extracts a bronchus region included in the lung region, a branching position information acquisition unit that acquires information of a branching position of the bronchus region, a reaching position information estimation unit that estimates reaching position information of a position at which an extended line of a branch included in the bronchus region reaches a surface of the lung region, based on the information of the branching position, and a display control unit that generates a mapping image in which the reaching position information is mapped to the surface of the lung region and that causes a display unit to display the mapping image.

In addition, in the mapping image display control device according to the aspect of the present invention, the reaching position information estimation unit can estimate, as the extended line of the branch, a straight line that is set based on the information of the branching position and an end of the branch.

In addition, in the mapping image display control device according to the aspect of the present invention, the reaching position information estimation unit can estimate, as the extended line of the branch, a straight line that is set based on the end of the branch and information of the first branching position from the end.

In addition, in the mapping image display control device according to the aspect of the present invention, the reaching position information estimation unit can perform spline interpolation by using a point on the branch and a point identified based on information of the first branching position from an end of the branch and can estimate a curved line determined by the spline interpolation as the extended line of the branch.

In addition, in the mapping image display control device according to the aspect of the present invention, the reaching position information estimation unit can identify the branch based on the information of the branching position, can identify a dominated region of the identified branch in the lung region, and can estimate, as the extended line of the branch, a straight line that links a centroid of the dominated region and an end of the branch.

In addition, in the mapping image display control device according to the aspect of the present invention, the reaching position information estimation unit can identify the branch based on the information of the branching position, can identify a dominated region of the identified branch in the lung region, and can estimate, as the reaching position information, a centroid of a region that is a surface of the dominated region and that also is the surface of the lung region.

In addition, the mapping image display control device according to the aspect of the present invention can include a blood vessel region extraction unit that extracts a blood vessel region included in the lung region, and the reaching position information estimation unit can estimate the extended line of the branch based on the blood vessel region and the information of the branching position.

In addition, in the mapping image display control device according to the aspect of the present invention, the blood vessel region extraction unit can extract, as the blood vessel region, at least one of a pulmonary vein region and a pulmonary artery region.

In addition, in the mapping image display control device according to the aspect of the present invention, the display control unit can set a region including a reaching position identified by the reaching position information, can generate a mapping image in which the region is mapped to the surface of the lung region, and can cause the display unit to display the mapping image.

A mapping image display control method according to an aspect of the present invention includes extracting a lung region included in a three-dimensional image, extracting a bronchus region included in the lung region, acquiring information of a branching position of the bronchus region, estimating reaching position information of a position at which an extended line of a branch included in the bronchus region reaches a surface of the lung region, based on the information of the branching position, and generating a mapping image in which the reaching position information is mapped to the surface of the lung region and causing a display unit to display the mapping image.

A computer readable non-transitory recording medium storing a mapping image display control program according to an aspect of the present invention causes a computer to function as a lung region extraction unit that extracts a lung region included in a three-dimensional image, a bronchus region extraction unit that extracts a bronchus region included in the lung region, a branching position information acquisition unit that acquires information of a branching position of the bronchus region, a reaching position information estimation unit that estimates reaching position information of a position at which an extended line of a branch included in the bronchus region reaches a surface of the lung region, based on the information of the branching position, and a display control unit that generates a mapping image in which the reaching position information is mapped to the surface of the lung region and that causes a display unit to display the mapping image.

With the mapping image display control device, method, and a computer readable non-transitory recording medium storing program according to the aspects of the present invention, a lung region included in a three-dimensional image is extracted, a bronchus region included in the lung region is extracted, and information of a branching position of the bronchus region is acquired. Then, based on the information of the branching position, reaching position information of a position at which an extended line of a branch included in the bronchus region reaches a surface of the lung region is estimated. Thus, a position which dye reaches in VAL-MAP described above can be simulated at a high accuracy. That is, even in the case where the extraction accuracy of a bronchial path is low and the end of the bronchial path bends in an unnatural direction as described above, reaching position information is estimated based on information of a branching position. Thus, a position which the dye reaches can be simulated at a high accuracy. Note that a method for estimating reaching position information based on information of a branching position will be described in detail later.

Further, a mapping image in which the reaching position information simulated at a high accuracy is mapped to the surface of the lung region can be generated and displayed.

DESCRIPTION OF THE PREFERRED EMBODIMENTS

Figure 1:
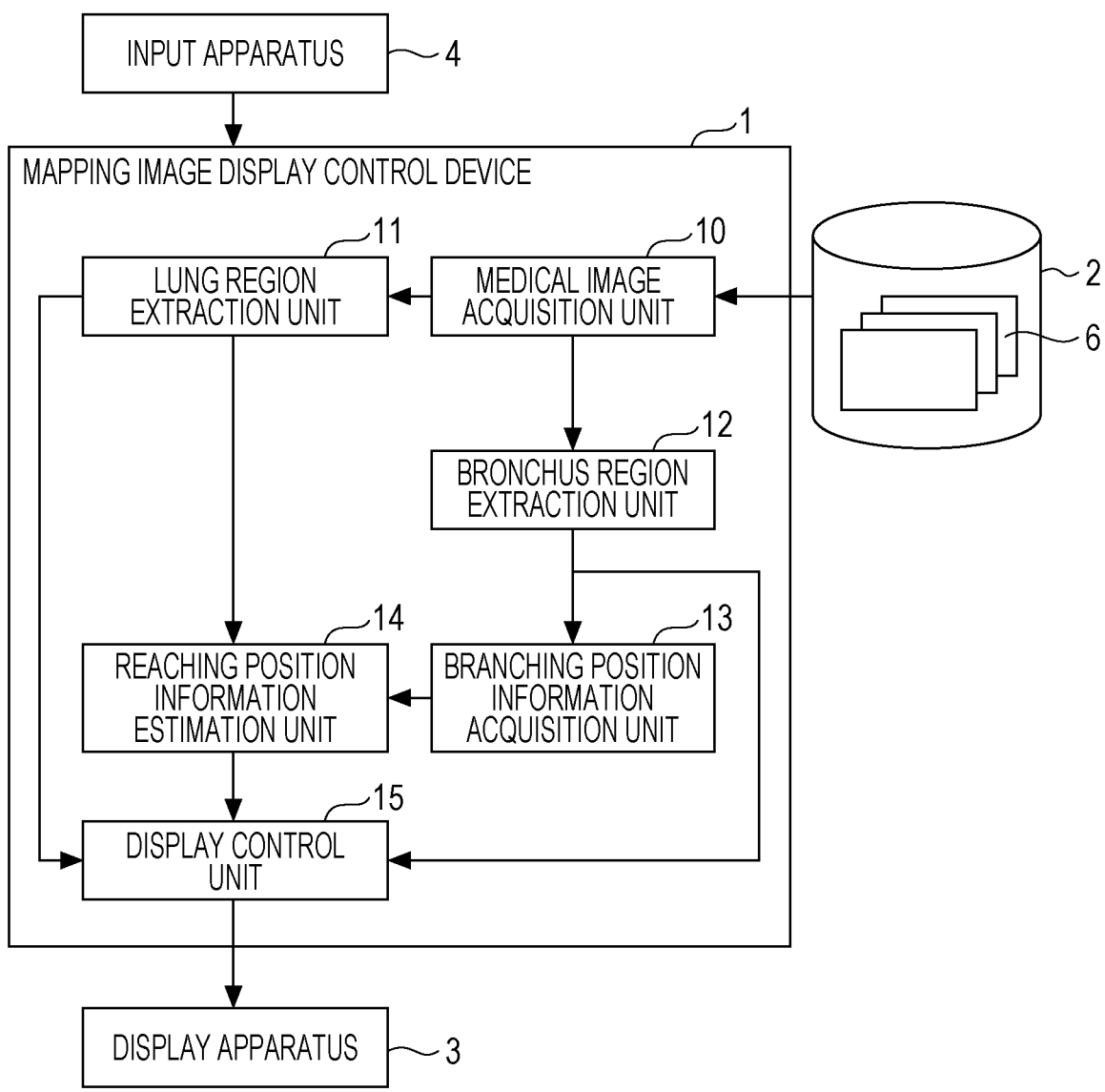
FIG. 1 is a block diagram illustrating a schematic configuration of a medical-image-diagnosis assisting system that uses an embodiment of a mapping image display control device, method, and a recording medium storing a program according to the present invention.

A medical-image-diagnosis assisting system that uses an embodiment of a mapping image display control device, method, and a recording medium storing a program according to the present invention will be described in detail below with reference to the drawings. FIG. 1 is a block diagram illustrating a schematic configuration of the medical-image-diagnosis assisting system according to the embodiment.

The medical-image-diagnosis assisting system according to the embodiment assists doctors when the doctors perform VAL-MAP described above. Specifically, the medical-image-diagnosis assisting system according to the embodiment simulates positions on the lung surface at which dye seeps if the dye is sprayed into the peripheries of bronchi and generates and displays a mapping image in which the positions are mapped to the lung surface. Since observation of this mapping image allows doctors to grasp which position on the lung surface the dye seeps if a bronchus is selected and the dye is sprayed into the periphery thereof, the doctors can appropriately select each bronchus into which the dye is to be sprayed prior to the procedure.

Specifically, as illustrated in FIG. 1, the medical-image-diagnosis assisting system according to the embodiment includes a mapping image display control device 1, a medical image storage server 2, a display apparatus 3 (corresponding to a display unit), and an input apparatus 4.

The mapping image display control device 1 is implemented by installing the mapping image display control program according to the embodiment on a computer.

The mapping image display control device 1 includes a CPU (central processing unit), a semiconductor memory, and a storage device such as a hard disk or an SSD (solid state drive). The mapping image display control program according to the embodiment is installed on the storage device. As a result of this mapping image display control program being executed by the CPU, a medical image acquisition unit 10, a lung region extraction unit 11, a bronchus region extraction unit 12, a branching position information acquisition unit 13, a reaching position information estimation unit 14, and a display control unit 15 illustrated in FIG. 1 operate.

The mapping image display control program is distributed after being recorded on a recording medium, such as a DVD (Digital Versatile Disc) or a CD-ROM (Compact Disc Read Only Memory), and is installed on the computer from the recording medium. Alternatively, the mapping image display control program is stored in a storage device of a server computer connected to a network or a network storage in an externally accessible state and is downloaded to and installed on the computer in response to a request.

The medical image acquisition unit 10 acquires three-dimensional images 6 of the thorax of patients obtained by imaging the patients in advance. The three-dimensional images 6 are obtained by imaging the thorax of patients by using a CT (computed tomography) apparatus or an MRI (magnetic resonance imaging) apparatus, for example.

The three-dimensional images 6 are stored in the medical image storage server 2 in advance, together with identification information of respective patients. On the basis of identification information of a patient input by the user by using the input apparatus 4 or the like, the medical image acquisition unit 10 reads out the three-dimensional image 6 having the identification information from the medical image storage server 2 and temporarily stores the three-dimensional image 6.

The lung region extraction unit 11 performs a process of extracting a lung region from the three-dimensional image 6 of the thorax acquired by the medical image acquisition unit 10. As a method for extracting a lung region, a publicly known method, such as a method for extracting a lung region by creating a histogram of signal values at respective pixel positions in the three-dimensional image 6 and processing the histogram using a threshold or a region growing method based on seed points representing a lung region, can be used since the lung fields are regions where air is present.

The bronchus region extraction unit 12 performs a process of extracting a bronchus region included in the lung region of the three-dimensional image 6 of the thorax. Bronchi included in the three-dimensional image 6 are assumed such that pixels for the inside of the bronchi are represented as regions showing low pixel values since they correspond to an air region but the bronchus walls are structures having a cylindrical column shape or a linear shape that show relatively high pixel values. Thus, a structural analysis of a shape based on a pixel value distribution is performed for individual pixels to extract bronchi. For example, as in a method described in JP2012-200403A, a bronchus region and a graph structure obtained by performing thinning on the bronchus region can be extracted by performing Hessian analysis based on pixel values of respective pixels. Note that another publicly known technique may be used as the method for extracting a bronchus region.

The branching position information acquisition unit 13 acquires information about a branching position of the bronchus region extracted by the bronchus region extraction unit 12. Specifically, the branching position information acquisition unit 13 classifies a graph structure of a bronchus region extracted by the bronchus region extraction unit 12 into a start point, an end point, a branching point, and an edge and acquires position information of the branching point as information about the branching position of the bronchus region.

The reaching position information estimation unit 14 estimates reaching position information about a position at which an extended line of a branch included in a bronchus region reaches the surface of the lung region on the basis of the information about the branching position acquired by the branching position information acquisition unit 13.

A position at which, if dye is sprayed into the periphery of a bronchus in VAL-MAP, the dye reaches the lung surface and seeps to the lung surface after passing through the lung tissue can be estimated as a position at which the extended line of the branch of the bronchus reaches the lung surface.

Accordingly, it is conceivable to extract a graph structure of a bronchus region from a three-dimensional image, set a straight line that links an end of a branch included in the graph structure and a point on an edge near the end (for example, a point immediately preceding the end) as an extended line of the branch, and estimate a position at which the extended line reaches the surface of the lung region as a position which the dye reaches (seeps).

However, the end of the branch sometimes has an irregular shape depending on the extraction accuracy of the graph structure. In such cases, if a straight line that links the end of the branch and the point on the edge near the end is set as the extended line of the branch in a manner as described above, the direction in which the extended line extends sometimes completely differs from the direction in which the branch of the bronchus region actually extends. As a result, the estimation accuracy of the reaching position of the dye may markedly decrease.

Figure 2:
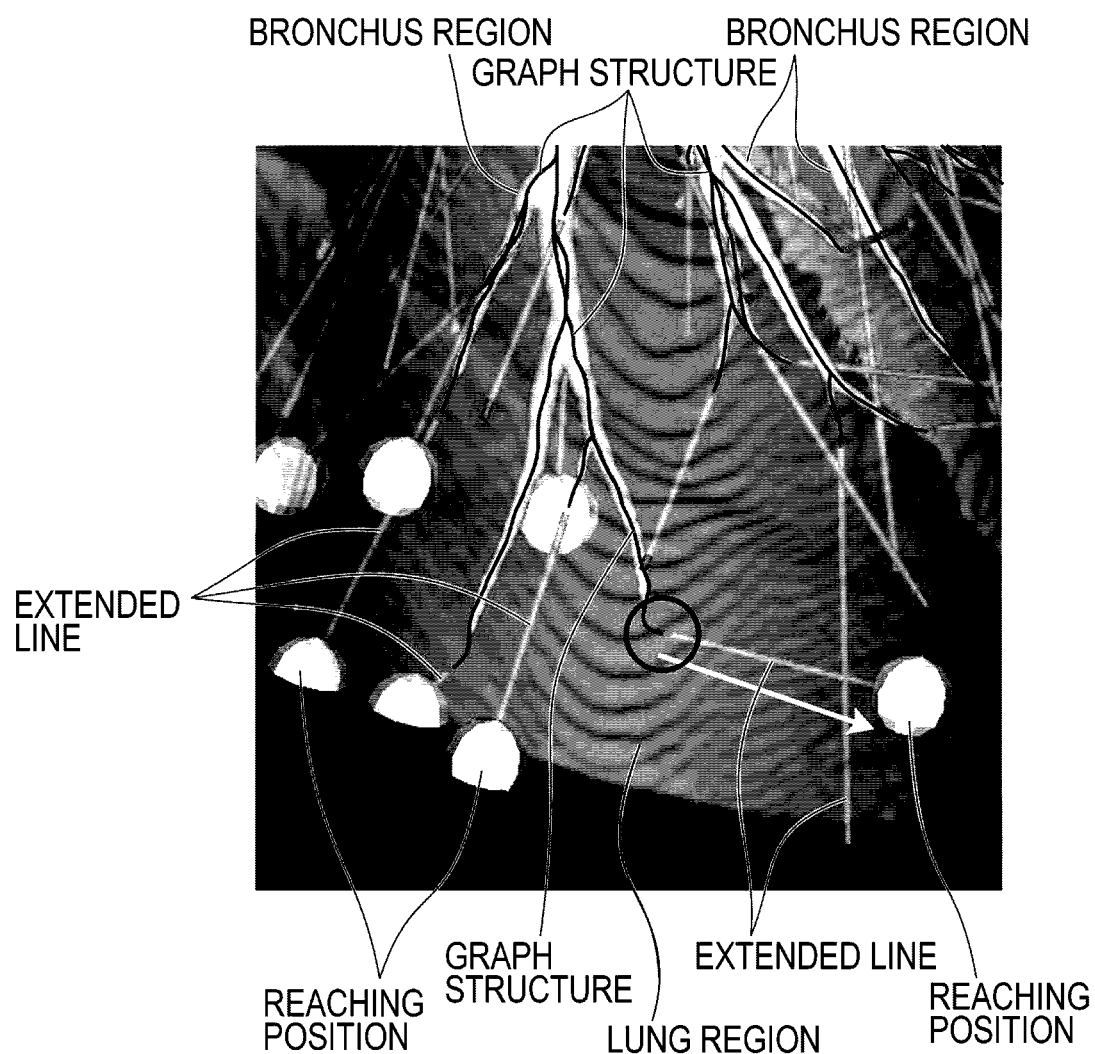
FIG. 2 is a diagram illustrating a case where an end of a graph structure acquired from a bronchus region has an irregular shape.

FIG. 2 is a diagram illustrating a case where the end of a branch of a graph structure has an irregular shape as described above. FIG. 2 illustrates a volume rendering image of a lung region and bronchus regions. FIG. 2 also illustrates the graph structures of the bronchus regions by using thin black lines and extended lines of branches of the graph structures by using thick gray lines. FIG. 2 further illustrates positions at which respective extended lines of the branches of the graph structures reach the surface of the lung region by using spheres or hemispheres. A portion near the end of the graph structure in a black-line circle illustrated in FIG. 2 is extracted to have a shape that bends to the right in the figure compared with the actual shape. As a result, the position which the dye is estimated to reach is shifted to the right (in a direction of a white arrow) in the figure compared with the position which the dye actually reaches.

Accordingly, the reaching position information estimation unit 14 according to the embodiment estimates a straight line that is set on the basis of information about a branching position acquired by the branching position information acquisition unit 13 and the end of a branch of a graph structure as an extended line of the branch of the bronchus region in order to solve the issue described above. The reaching position information estimation unit 14 according to the embodiment then estimates reaching position information about a position at which the extended line reaches the surface of the lung region as a position at which the dye reaches the lung surface.

Figure 3:
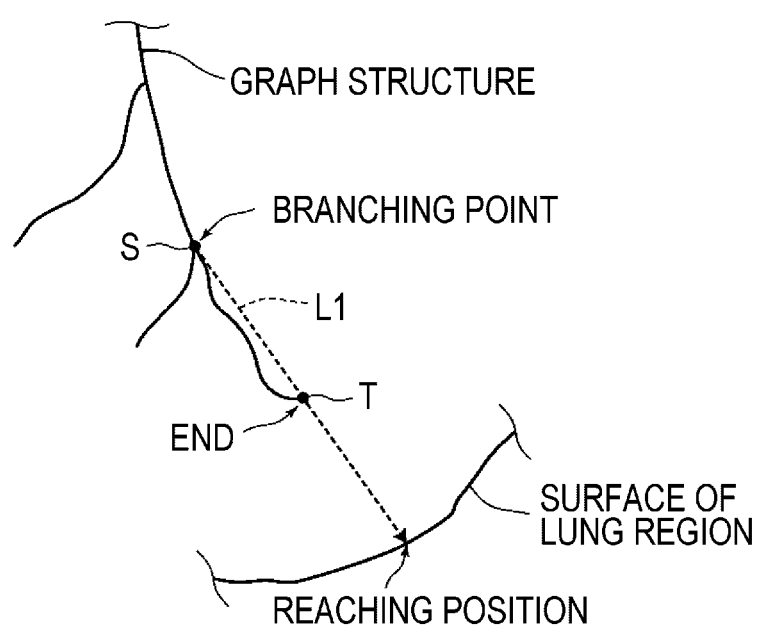
FIG. 3 is a diagram for describing a case where a straight line that links an end of a branch of a graph structure of a bronchus region and the first branching point from the end is estimated as an extended line of the branch of the bronchus region.

Specifically, the reaching position information estimation unit 14 estimates a straight line that links an end T of a branch of a graph structure of a bronchus region and a first branching point S from the end T as an extended line L1 of the branch of the bronchus region as illustrated in FIG. 3. The reaching position information estimation unit 14 then acquires the intersection of the extended line L1 and the surface of the lung region as reaching position information. The first branching point from the end T refers to the first branch in a direction from the end of the bronchus region to the upstream side of the bronchus.

Although the first branching point from the end T is used in the embodiment, the branching point to be used is not limited to this one. The second or third branching point from the end T may be used.

In addition, although the end T of the branch of the graph structure of the bronchus region is linked to the first branching point S from the end T in the embodiment, the branching point S need not necessarily be used. Any point near the branching point S may be used as long as substantially the same result is obtained with the point. That is, a straight line that is set on the basis of the information about the branching position and the end of the branch of the graph structure includes a straight line that is set by linking the end T of the branch and a point near the branching point S.

In addition, although the reaching position information estimation unit 14 according to the embodiment acquires an intersection of an extended line of a branch of a bronchus region and the surface of the lung region as reaching position information, the reaching position information need not necessarily represent coordinates of a single point. A two-dimensional or three-dimensional range including the intersection may be acquired as reaching position information. Reaching position information acquired by the reaching position information estimation unit 14 is information representing a reaching point or reaching range at which, if dye is sprayed into the periphery of a bronchus, the dye reaches the lung surface after passing through the lung tissue.

The display control unit 15 generates a volume rendering image of the lung region and the bronchus regions on the basis of the lung region extracted by the lung region extraction unit 11 and the bronchus regions extracted by the bronchus region extraction unit 12. Opacity of the volume rendering image of the lung region is set such that the bronchus regions in the lung region are visually recognizable, and the color for the lung region and the color for the bronchus regions are set to be different.

In addition, the display control unit 15 causes the display apparatus 3 to display a mapping image in which the graph structures obtained by performing thinning on the bronchus regions and the extended lines of the branches of the bronchus regions and pieces of reaching position information set by the reaching position information estimation unit 14 are superimposed on the volume rendering image of the lung region and the bronchus regions.

Figure 4:
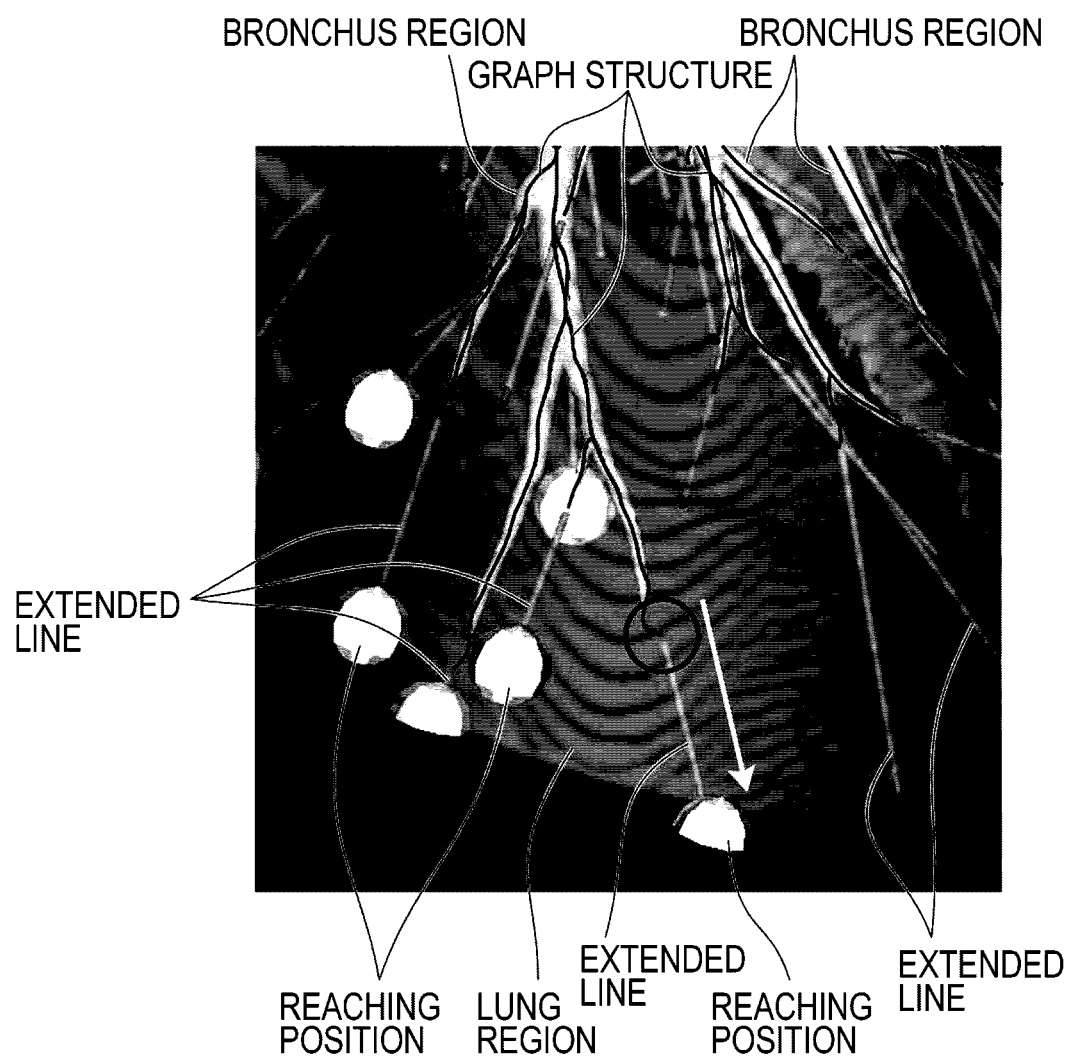
FIG. 4 is a diagram illustrating an example of a mapping image generated by the medical-image-diagnosis assisting system that uses an embodiment of the mapping image display control device, method, and a recording medium storing a program according to the present invention.

FIG. 4 is a diagram illustrating an example of a mapping image displayed by the display apparatus 3. As illustrated in FIG. 4, a graph structure of each bronchus region is represented using a thin black line, an extended line of a branch of each bronchus region is represented using a thick gray line, and reaching position information is represented using a sphere or hemisphere. As illustrated in FIG. 4, a portion near the end of the graph structure in a black-line circuit has a shape that bends to the right in the figure compared with the actual shape. However, FIG. 4 indicates that an extended line of the bronchus region is set in a direction identical to the extending direction of the branch of the bronchus region and the position at which the dye reaches the lung surface is estimated at a high accuracy. Note that a sphere or hemisphere representing reaching position information corresponds to a region including the reaching position identified by the reaching position information in accordance with the present invention.

In addition, the size of the sphere or hemisphere representing reaching position information and displayed in the mapping image can be set by the user in a given manner by using the input apparatus 4. In addition, display and non-display of the sphere or hemisphere representing reaching position information may be switched between or the sphere or hemisphere representing reaching position information may be displayed to flash on and off. Further, the extended lines of the bronchus regions need not necessarily be displayed, and display and non-display thereof may be switched between by the user.

The display apparatus 3 includes a display device such as a liquid crystal display. The display apparatus 3 displays the above-described volume rendering image or the like.

The input apparatus 4 receives various inputs for setting from the user and includes input devices such as a keyboard and a mouse. The input apparatus 4 receives, for example, an input for setting identification information of a patient, an input for setting the opacity and color of the volume rendering image, and an input for setting the displayed shape and size of the reaching position information. Note that a touch panel may be used as both the display apparatus 3 and the input apparatus 4.

Figure 5:
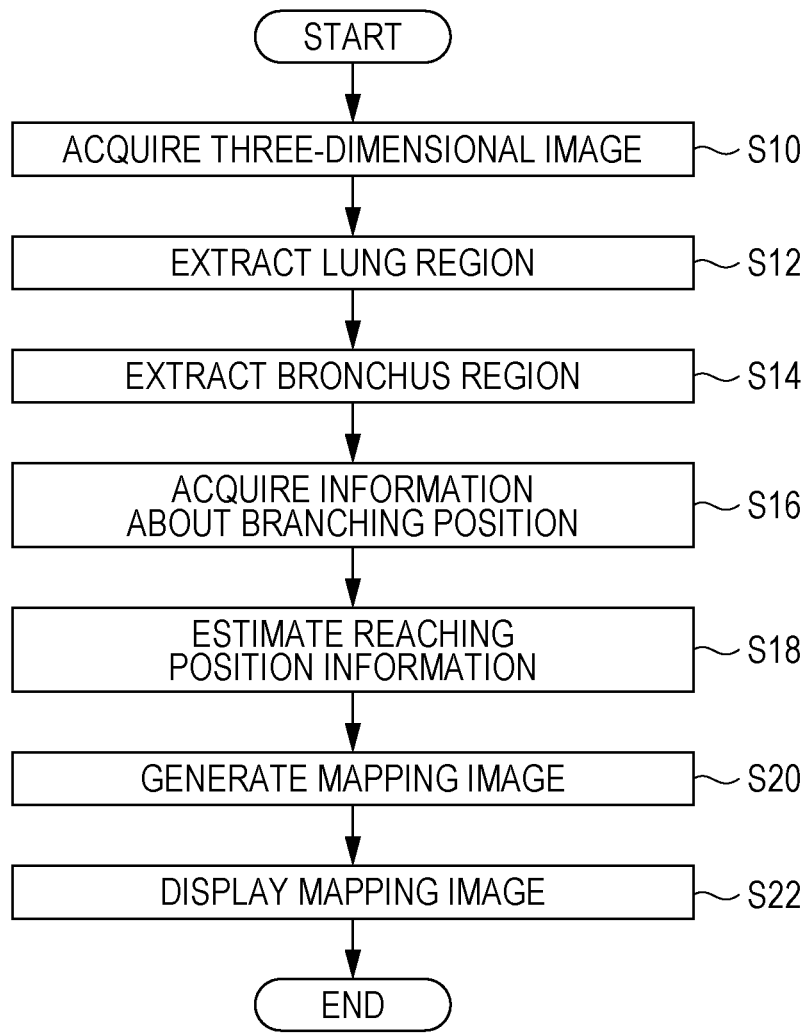
FIG. 5 is a flowchart for describing an operation of the medical-image-diagnosis assisting system that uses an embodiment of the mapping image display control device, method, and a recording medium storing a program according to the present invention.

An operation of the medical-image-diagnosis assisting system according to the embodiment will be described next with reference to a flowchart illustrated in FIG. 5.

First, the medical image acquisition unit 10 reads out and acquires the three-dimensional image 6 from the medical image storage server 2 in accordance with identification information of a patient or the like input by the user (S10).

The three-dimensional image 6 acquired by the medical image acquisition unit 10 is input to the lung region extraction unit 11 and the bronchus region extraction unit 12. The lung region extraction unit 11 extracts each lung region from the input three-dimensional image 6 (S12). The bronchus region extraction unit 12 extracts bronchus regions from the input three-dimensional image 6 and further acquires graph structures by performing thinning on the bronchus regions (S14).

The graph structures acquired by the bronchus region extraction unit 12 are input to the branching position information acquisition unit 13. The branching position information acquisition unit 13 acquires information about a branching position of each bronchus region on the basis of the input graph structures (S16).

The information about the branching position acquired by the branching position information acquisition unit 13 is input to the reaching position information estimation unit 14. The reaching position information estimation unit 14 sets an extended line of a branch of each bronchus region on the basis of the input information about the branching position and acquires an intersection of the extended line and the surface of the lung region as reaching position information (S18).

The lung region extracted by the lung region extraction unit 11 and the bronchus regions extracted by the bronchus region extraction unit 12 are input to the display control unit 15. The display control unit 15 generates a volume rendering image of the lung region and the bronchus regions on the basis of the input lung region and bronchus regions. Further, the graph structures obtained by performing thinning on the bronchus regions and the extended lines of branches of the bronchus regions and the reaching position information set by the reaching position information estimation unit 14 are input to the display control unit 15. The display control unit 15 generates a mapping image in which the input graph structures, extended lines of the branches, and reaching position information are superimposed on the volume rendering image of the lung region and the bronchus regions (S20) and causes the display apparatus 3 to display the mapping image (S22).

With the medical-image-diagnosis assisting system according to the embodiment, a lung region included in a three-dimensional image is extracted, a bronchus region included in the lung region is extracted, and information about a branching position of the bronchus region is acquired. Then, reaching position information about a position at which an extended line of a branch included in the bronchus region reaches the surface of the lung region is estimated on the basis of the information about the branching position. Thus, a position which dye reaches in VAL-MAP described above can be simulated at a high accuracy. That is, even if the extraction accuracy of the graph structure is low and the end of the graph structure bends in an unnatural direction as described above, a position which dye reaches can be simulated at a high accuracy because the reaching position information is estimated on the basis of the information about the branching position.

In addition, a mapping image in which reaching position image that is simulated at a high accuracy is mapped to the surface of the lung region can be generated and displayed.

Further, since a straight line that links the end T and the first branching point S from the end T is estimated as the extended line L1 of the branch of the bronchus region in the embodiment, the extended line L1 can be estimated by a simple calculation process.

Figure 6:
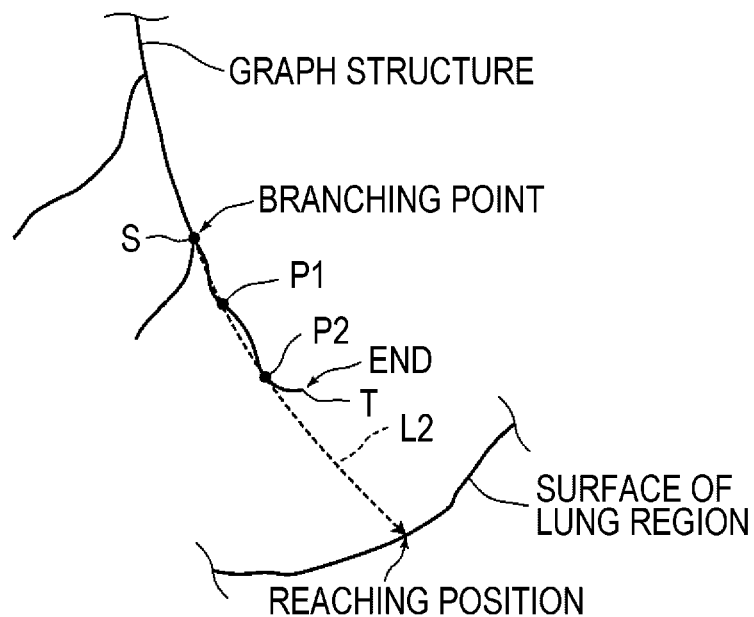
FIG. 6 is a diagram for describing a case where a curved line obtained by performing spline interpolation using two points on a branch and a branching point is estimated as an extended line of the branch of the bronchus region.

In the embodiment above, a straight line that links an end of a graph structure and a branching point is estimated as an extended line of the branch of the bronchus region. However, the method for setting an extended line of a branch of a bronchus region is not limited to this one. For example, as illustrated in FIG. 6, spline interpolation may be performed by using two points P1 and P2 on a branch and the first branching point S from the end T of the branch, and a curved line L2 determined by the spline interpolation may be estimated as an extended line of the branch of the bronchus region.

In the case where the curved line L2 determined by spline interpolation is estimated as the extended line of the branch of the bronchus region in this way, the extended line of the branch can be estimated at a higher accuracy.

Note that the branching point S need not necessarily be used also in the case where the extended line of the branch is estimated by spline interpolation in this manner. Any point near the branching point S may be used as long as substantially the same result is obtained with the point.

Figure 7:
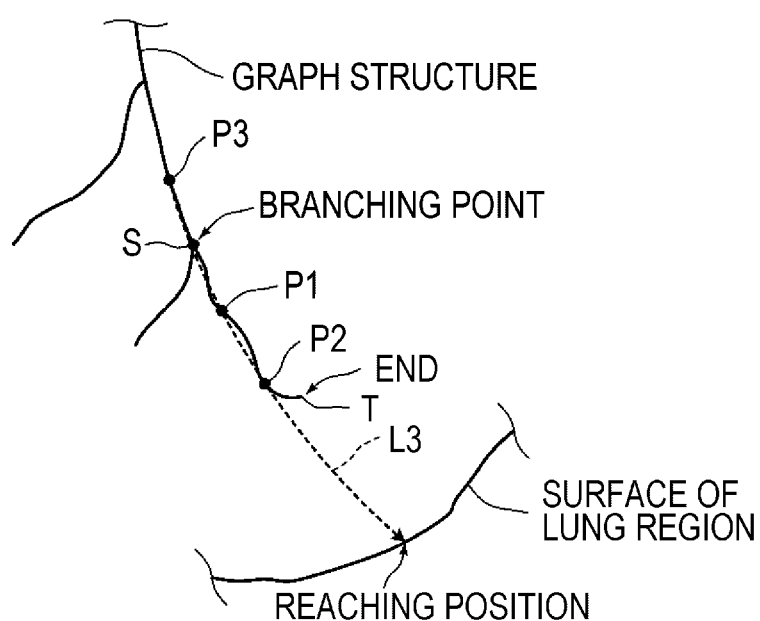
FIG. 7 is a diagram for describing another example of the case where the extended line of the branch of the bronchus region is estimated by spline interpolation.

In addition, in the description above, spline interpolation is performed by using the branching point S and the two points P1 and P2 on the branch. However, as for points other than the branching point S, three or more points may be set. In addition, instead of setting two points on the branch as illustrated in FIG. 6, spline interpolation may be performed by using at least one or more points P1 on the branch, the branching point S, and a point P3 located on the upstream side of the branching point S in the bronchus to estimate a curved line L3 as illustrated in FIG. 7. The point P3 is desirably set between the branching point S and a branching point that immediately precedes the branching point S on the upstream side in the bronchus. The points P1 to P3 used in spline interpolation may be set by the user in a given manner by using the input apparatus 4 or may be automatically set by setting a distance from the branching point S in advance.

In addition, a branch may be identified on the basis of information about a branching position acquired by the branching position information acquisition unit 13, a dominated region of the identified branch in the lung region may be identified, and a straight line that links the centroid of the dominated region and the end of the branch may be estimated as an extended line of the branch of the bronchus region.

Figure 8:
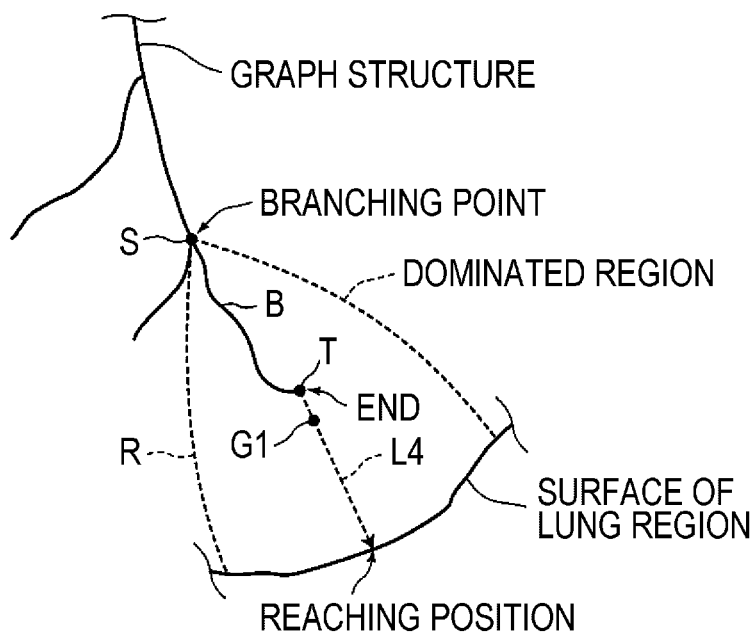
FIG. 8 is a diagram for describing a case where a straight line that links the centroid of a dominated region of a branch and an end of the branch is estimated as an extended line of the branch of the bronchus region.

Specifically, as illustrated in FIG. 8, a branch B may be identified on the basis of the branching point S acquired by the branching position information acquisition unit 13, a dominated region R of the branch B in the lung region may be identified, and a straight line L4 that links a centroid G1 of the dominated region R and the end T of the branch B may be estimated as an extended line of the branch of the bronchus region. Note that a dominated region of a branch of a bronchus region is set in advance for each branch from the anatomical viewpoint, and the centroid G1 in this case is a centroid of the dominated region having a three-dimensional shape in a three-dimensional space.

In the case where the straight line L4 that links the centroid G1 of the dominated region R and the end T of the branch B is estimated as the extended line of the branch of the bronchus region, the extended line of the branch can be estimated at a higher accuracy in accordance with the anatomical viewpoint.

In addition, as another method for estimating a reaching position at which an extended line of a branch reaches the lung surface by using a dominated region of the branch of the bronchus region in a manner described above, a branch may be identified on the basis of the information about the branching position acquired by the branching position information acquisition unit 13, a dominated region of the identified branch in the lung region may be identified, and the centroid of a region that is the surface of the dominated region and that also is the surface of the lung region may be estimated as reaching position information, for example.

Figure 9:
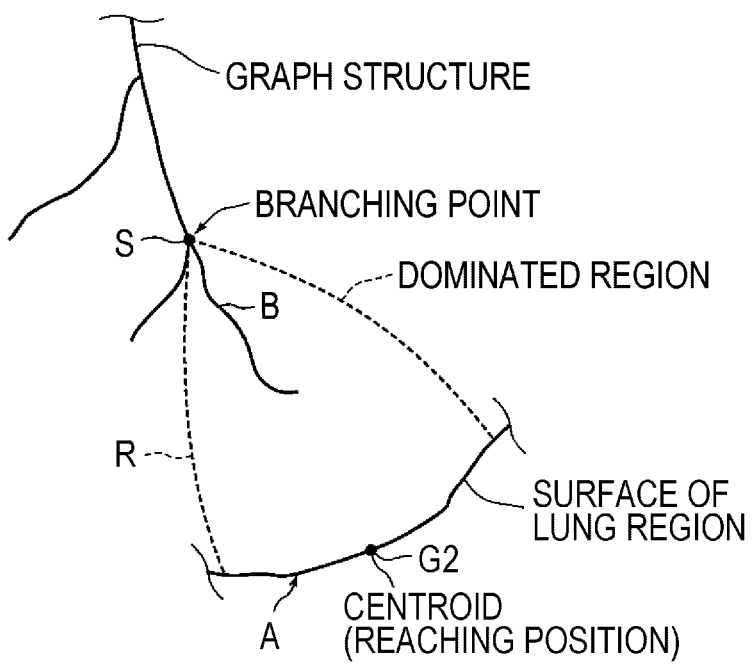
FIG. 9 is a diagram for describing a case where the centroid of a region that is the surface of the dominated region and that also is the surface of the lung region is estimated as reaching position information.

Specifically, as illustrated in FIG. 9, the branch B may be identified on the basis of the branching point S acquired by the branching position information acquisition unit 13, the dominated region R of the branch B in the lung region may be identified, and a centroid G2 of a region A that is the surface of the dominated region R and that also is the surface of the lung region may be estimated as reaching position information. Note that the centroid G2 in this case is a centroid of the region A that is represented as a plane in the three-dimensional space.

In addition, it is known that the pulmonary artery and the pulmonary vein are located near the bronchi and extending directions of the bronchi and extending directions of the pulmonary artery and the pulmonary vein are similar to each other. Thus, a position at which an extended line of a branch of a bronchus region reaches the lung surface may be estimated on the basis of information about the extending direction of the pulmonary artery or the pulmonary vein.

Figure 10:
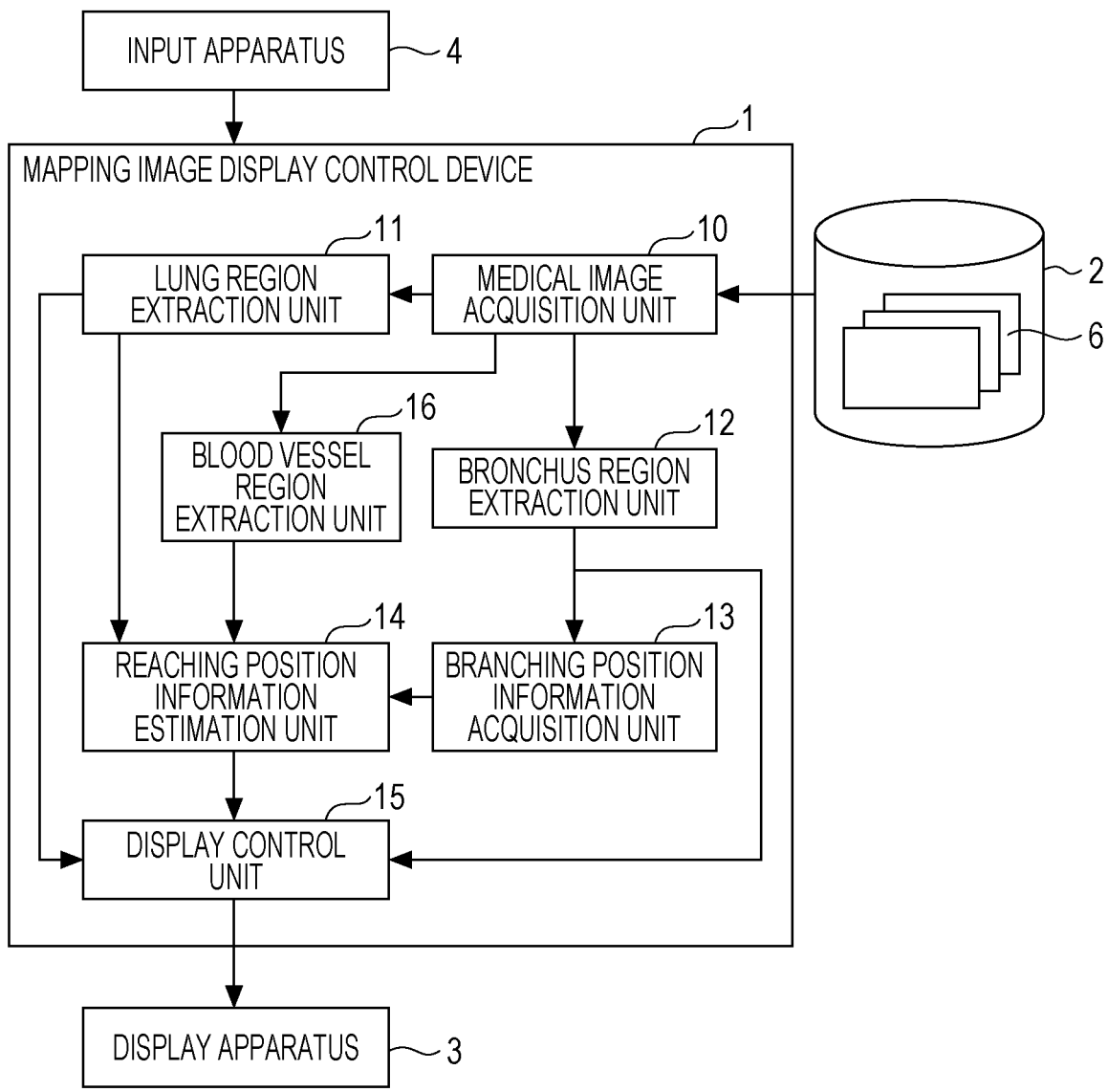
FIG. 10 is a block diagram illustrating a schematic configuration of the medical-image-diagnosis assisting system that further includes a blood vessel region extraction unit.

Specifically, a blood vessel region extraction unit 16 is further provided in the mapping image display control device 1 as illustrated in FIG. 10. The blood vessel region extraction unit 16 extracts a blood vessel region included in the lung region from the three-dimensional image 6. Specifically, the blood vessel region extraction unit 16 extracts a pulmonary artery region and a pulmonary vein region. As an extraction method of the pulmonary artery region and the pulmonary vein region, a publicly know technique, for example, a region growing method, can be used.

Figure 11:
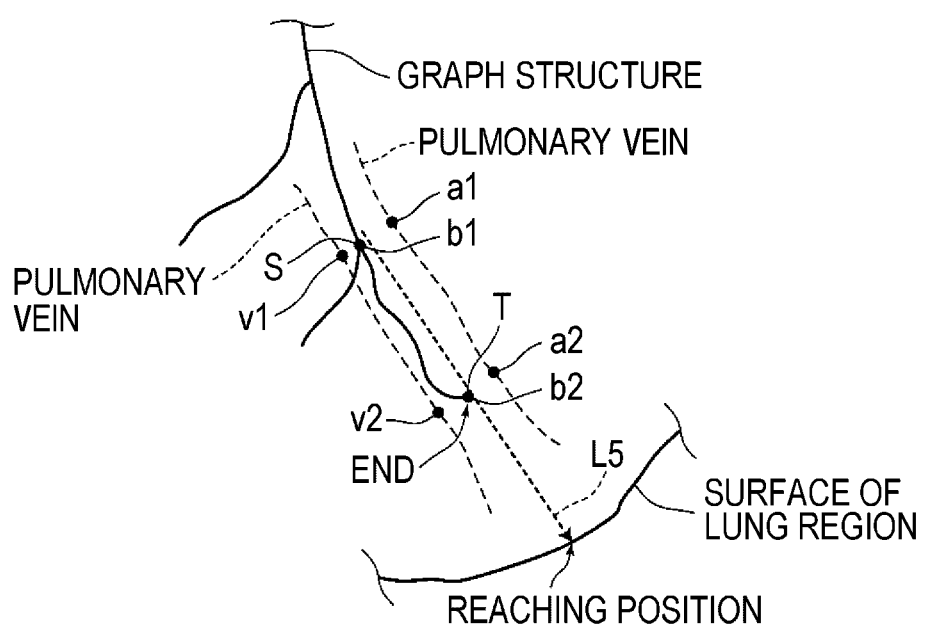
FIG. 11 is a diagram for describing a case where a position at which an extended line of a branch of a bronchus region reaches the lung surface is estimated on the basis of a blood vessel region and information about a branching position.

Then, the reaching position information estimation unit 14 identifies a pulmonary artery region and a pulmonary vein region that extend along a branch of a bronchus region on the basis of information about a branching position acquired by the branching position information acquisition unit 13 and estimates an extended line of the branch of the bronchus region on the basis of the identified pulmonary artery region and pulmonary vein region. Specifically, as illustrated in FIG. 11, a position v1 in a pulmonary artery region that is the closest to the branching point S acquired by the branching position information acquisition unit 13 and a position a1 in a pulmonary vein region that is the closest to the branching point S are detected. Further, a position v2 in the pulmonary artery region that is the closest to the end T of the branch of the graph structure and a position a2 in the pulmonary vein region that is the closest to the end T are detected.

Note that the branching point S is the first branching point from the end T of the branch of the graph structure on the upstream side in the bronchus. In addition, the position v1 in the pulmonary artery region that is the closest to the branching point S is a position whose distance to the branching point S is the shortest in the pulmonary artery region, and the position a1 in the pulmonary vein region that is the closest to the branching point S is a position whose distance to the branching point S is the shortest in the pulmonary vein region. In addition, the position v2 in the pulmonary artery region that is the closest to the end T is a position whose distance to the end T is the shortest in the pulmonary artery region, and the position a2 in the pulmonary vein region that is the closest to the end T is a position whose distance to the end T is the shortest in the pulmonary vein region.

Then, a direction from the position v1 to the position v2 in the pulmonary artery region is estimated as an extending direction of the pulmonary artery region, and a first vector is set. A direction from the position a1 to the position a2 in the pulmonary vein region is estimated as an extending direction of the pulmonary vein region, and a second vector is set. An average of the first vector and the second vector is calculated. Then, a straight line L5 obtained by extending the average vector is estimated as the extended line of the branch of the bronchus region, and the position at which this extended line reaches the lung surface is acquired.

By estimating an extended line of a branch by using the pulmonary vein region and the pulmonary artery region in this way, the extended line of the branch can be estimated at a higher accuracy in accordance with the anatomical viewpoint.

In the description above, the first vector is set by using the positions v1 and v2 in the pulmonary artery region and the second vector is set by using the positions a1 and a2 in the pulmonary vein region. Alternatively, for example, spline interpolation may be performed by using the positions v1 and v2 in the pulmonary artery region and a point between these positions to set a first curved line, and spline interpolation may be performed by using the positions a1 and a2 in the pulmonary vein region and a point between these positions to set a second curved line. An average curved line of the first curved line and the second curved line may be estimated as the extended line of the branch of the bronchus region.

In addition, in the description above, an extended line of a branch is estimated by using both the pulmonary vein region and the pulmonary artery region. However, the extended line of the branch may be estimated by using only one of the pulmonary vein region and the pulmonary artery region. For example, a straight line that is parallel to the first vector set on the basis of the pulmonary artery region and that passes through the end T of the branch may be estimated as the extended line of the branch. Alternatively, a straight line that is parallel to the second vector set on the basis of the pulmonary vein region and that passes through the end T of the branch may be estimated as the extended line of the branch.

REFERENCE SIGNS LIST

1 mapping image display control device
2 medical image storage server
3 display apparatus
4 input apparatus
10 medical image acquisition unit
11 lung region extraction unit
12 bronchus region extraction unit
13 branching position information acquisition unit
14 reaching position information estimation unit
15 display control unit
16 blood vessel region extraction unit

What is claimed is:

1. A mapping image display control device comprising:
a processor configured to
  extract a lung region included in a three-dimensional image;
  extract a bronchus region included in the lung region;
  acquire information of a branching position of the bronchus region;
  estimate reaching position information of a position at which an extended line of a branch included in the bronchus region reaches a surface of the lung region, based on the information of the branching position;
wherein the processor configured to identify the branch based on the information of the branching position, identify a dominated region of the identified branch in the lung region, and estimate, as the extended line of the branch, a straight line that links a centroid of the dominated region and an end of the branch; and
  generate a mapping image in which the reaching position information is mapped to the surface of the lung region and that causes a display unit to display the mapping image.

2. The mapping image display control device according to claim 1, wherein the processor estimates, as the extended line of the branch, a straight line that is set based on the information of the branching position and an end of the branch.

3. The mapping image display control device according to claim 2, wherein the processor estimates, as the extended line of the branch, a straight line that is set based on the end of the branch and information of a first branching position from the end.

4. The mapping image display control device according to claim 3, wherein the processor sets a region including a reaching position identified by the reaching position information, generates a mapping image in which the region is mapped to the surface of the lung region, and causes the display unit to display the mapping image.

5. The mapping image display control device according to claim 2, wherein the processor sets a region including a reaching position identified by the reaching position information, generates a mapping image in which the region is mapped to the surface of the lung region, and causes the display unit to display the mapping image.

6. The mapping image display control device according to claim 1, wherein the processor performs spline interpolation by using a point on the branch and a point identified based on information of a first branching position from an end of the branch and estimates a curved line determined by the spline interpolation as the extended line of the branch.

7. The mapping image display control device according to claim 6, wherein the processor sets a region including a reaching position identified by the reaching position information, generates a mapping image in which the region is mapped to the surface of the lung region, and causes the display unit to display the mapping image.

8. The mapping image display control device according to claim 1, wherein the processor sets a region including a reaching position identified by the reaching position information, generates a mapping image in which the region is mapped to the surface of the lung region, and causes the display unit to display the mapping image.

9. The mapping image display control device according to claim 1, wherein the processor identifies the branch based on the information of the branching position, identifies a dominated region of the identified branch in the lung region, and estimates, as the reaching position information, a centroid of a region that is a surface of the dominated region and that also is the surface of the lung region.

10. The mapping image display control device according to claim 9, wherein the processor sets a region including a reaching position identified by the reaching position information, generates a mapping image in which the region is mapped to the surface of the lung region, and causes the display unit to display the mapping image.

11. The mapping image display control device according to claim 1, the processor further configured to:
extract a blood vessel region included in the lung region, wherein the processor estimates the extended line of the branch based on the blood vessel region and the information of the branching position.

12. The mapping image display control device according to claim 11, wherein the processor extracts, as the blood vessel region, at least one of a pulmonary vein region and a pulmonary artery region.

13. The mapping image display control device according to claim 12, wherein the processor sets a region including a reaching position identified by the reaching position information, generates a mapping image in which the region is mapped to the surface of the lung region, and causes the display unit to display the mapping image.

14. The mapping image display control device according to claim 1, wherein the processor sets a region including a reaching position identified by the reaching position information, generates a mapping image in which the region is mapped to the surface of the lung region, and causes the display unit to display the mapping image.

15. A mapping image display control method comprising:
extracting a lung region included in a three-dimensional image;
extracting a bronchus region included in the lung region;
acquiring information of a branching position of the bronchus region;
estimating reaching position information of a position at which an extended line of a branch included in the bronchus region reaches a surface of the lung region, based on the information of the branching position;
identifying the branch based on the information of the branching position, identifying a dominated region of the identified branch in the lung region, and estimating, as the extended line of the branch, a straight line that links a centroid of the dominated region and an end of the branch; and
generating a mapping image in which the reaching position information is mapped to the surface of the lung region and causing a display unit to display the mapping image.

16. A computer readable non-transitory recording medium storing a mapping image display control program causing a computer to function as:
a lung region extraction unit that extracts a lung region included in a three-dimensional image;
a bronchus region extraction unit that extracts a bronchus region included in the lung region;
a branching position information acquisition unit that acquires information of a branching position of the bronchus region;
a reaching position information estimation unit that estimates reaching position information of a position at which an extended line of a branch included in the bronchus region reaches a surface of the lung region, based on the information of the branching position;
wherein the reaching position information estimation unit identifies the branch based on the information of the branching position, identifies a dominated region of the identified branch in the lung region, and estimates, as the extended line of the branch, a straight line that links a centroid of the dominated region and an end of the branch; and
a display control unit that generates a mapping image in which the reaching position information is mapped to the surface of the lung region and that causes a display unit to display the mapping image.

17. A mapping image display control device comprising:
a processor configured to
extract a lung region included in a three-dimensional image;
extract a bronchus region included in the lung region;
acquire information of a branching position of the bronchus region;
estimate reaching position information of a position at which an extended line of a branch included in the bronchus region reaches a surface of the lung region, based on the information of the branching position;
wherein the processor configured to identify the branch based on the information of the branching position, identify a dominated region of the identified branch in the lung region, and estimate, as the reaching position information, a centroid of a region that is a surface of the dominated region and that also is the surface of the lung region; and generate a mapping image in which the reaching position information is mapped to the surface of the lung region and that causes a display unit to display the mapping image.

\* \* \* \* \*